United States Patent [19]

Ferruti et al.

[11] Patent Number: 5,698,661
[45] Date of Patent: Dec. 16, 1997

[54] HIGH MOLECULAR WEIGHT POLYESTERPOLYCARBONATES AND THE USE THEREOF FOR THE PREPARATION OF BIOEROSIBLE MATRICES

[75] Inventors: Paolo Ferruti; Maurizio Penco; Elisabetta Ranucci; Fabio Bignotti, all of Milan, Italy

[73] Assignee: ASTA Medica Aktiengesellschaft, Dresden, Germany

[21] Appl. No.: 637,646
[22] PCT Filed: Oct. 28, 1994
[86] PCT No.: PCT/EP94/03560
§ 371 Date: Jun. 24, 1996
§ 102(e) Date: Jun. 24, 1996
[87] PCT Pub. No.: WO95/12629
PCT Pub. Date: May 11, 1995

[30] Foreign Application Priority Data

Nov. 5, 1993 [IT] Italy ................. MI93A2364

[51] Int. Cl.⁶ .................................................. C08G 63/08
[52] U.S. Cl. .......................... 528/354; 427/2; 523/105; 523/113; 524/381; 528/176; 528/196; 528/361
[58] Field of Search ..................... 427/2; 523/105, 523/113; 524/381; 528/354, 361, 176, 196

[56] References Cited

U.S. PATENT DOCUMENTS 4,705,820 11/1987 Wang et al. .................. 524/381

FOREIGN PATENT DOCUMENTS

0427185A2 11/1990 European Pat. Off. .
WO 92/22600 12/1992 WIPO .

OTHER PUBLICATIONS

1297a Macromolecular Rapid Communications 15 (1994) Sep., No. 9, Zug, CH, "New High–molecular–weight poly9ester–carbonates) by chain extension of . . . " by M. Penco et al.

*Primary Examiner*—Terressa Mosley
*Attorney, Agent, or Firm*—Pennie & Edmonds

[57] ABSTRACT

Polyesterpolycarbonates of formula (I)

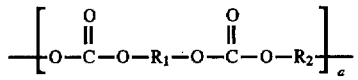

wherein a is an integer from 2 to 300; $R_1$ and $R_2$, which can be the same or different, are each a polyester residue of formula (II)

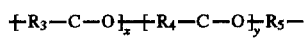

with x and y being integers from 0 to 100, and the ratio of $(x/x+y)*100$ being between 0 and 100, with the proviso that x and y are not 0 at the same time; $R_3$ and $R_4$ being aliphatic hydrocarbon residues of 1 to 4 carbon atoms; $R_5$ being an aliphatic hydrocarbon residue having from 2 to 18 carbon atoms or a cycloaliphatic hydrocarbon residue having from 3 to 8 carbon atoms; or a polyoxyalkylene residue of formula (III):

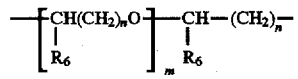

wherein $R_6$ is hydrogen or methyl, n is an integer from 1 to 3 and m is an integer from 1 to 200; and the two —$R_3$—COO and —$R_4$—COO groups are randomly distributed in the polyester residue, with the polyesterpolycarbonates of formula (I) having an intrinsic viscosity of greater than 0.45 dl/g when measured in chloroform at 32° C. and being useful as bioerosible matrices for the controlled release of drugs.

13 Claims, No Drawings

HIGH MOLECULAR WEIGHT POLYESTERPOLYCARBONATES AND THE USE THEREOF FOR THE PREPARATION OF BIOEROSIBLE MATRICES

The present invention relates to polyesterpolycarbonates of general formula (I)

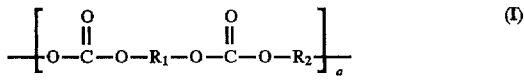

wherein a is an integer from 2 to 300; $R_1$ and $R_2$, which can be the same or different, are each a polyester residue of formula (II)

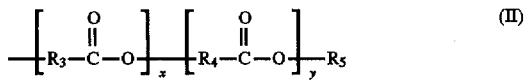

wherein x and y are integers from 0 to 100, the ratio (x/x+y)*100, being comprised between 0 and 100, with the proviso that x and y are not 0 at the same time; $R_3$ and $R_4$, which can be the same or different, are each a straight or branched chain aliphatic hydrocarbon residue having from 1 to 4 carbon atoms; $R_5$ is a straight or branched chain aliphatic hydrocarbon residue having from 2 to 18 carbon atoms or a cycloaliphatic hydrocarbon residue having from 3 to 8 carbon atoms, optionally bearing one or more straight or branched alkyl substituents; or it is a polyoxyalkylene residue of formula (III):

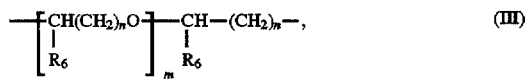

wherein: $R_6$ is hydrogen or methyl, n is an integer from 1 to 3 and m is an integer from 1 to 200; the two —$R_3$—COO and —$R_4$—COO groups being randomly distributed in the polyester residue, with the proviso that the polyesterpolycarbonates of formula (I) have intrinsic viscosity not lower than 0.45 dl/g.

Generally, the polymers used as carriers for controlled release drugs must be biocompatible, non toxic, free from impurities. Particularly, biodegradable polymers must give non-toxic, non-cancerogenic, non-teratogenic degradation products and must be easily eliminated.

The factors which affect biodegradability are chemical structure, morphology and particle size. Among these factors, crystallinity plays an important role, in view both of biodegradability and technology of polymer processing.

The common microencapsulation techniques comprise coacervation, evaporation of the emulsified solvent, coextrusion. The latter is the preferred technique since it avoids the use of solvents and accordingly implies no toxicologic problems due to solvent residues.

Extrudible polymers must be stable at the coextrusion temperature, have a softening point nor too high, to avoid drug decomposition, nor too low, to avoid storage problems.

Examples of pharmaceutical formulations, in which the drug (active ingredient) is incorporated in a biodegradable matrix, are well known in the art. Reference may be made to "Biodegradable Polymers as Drug Delivery Systems", ed. by M. Chasin and R. Langer, Marcel Drekker Inc., Orlando, Fla., 1985; "Formes Pharmaceutiques Nouvelles", P. Buri, F. Puisieux, E. Dalker, J. P. Benoît, Technique and documentation (Lavoisier), Paris, 1985; "Biodegradable Polymers for controlled Release of Peptides and Proteins", F. G. Hutchison and B. J. A. Furr, in Drug Carrier Systems, F. H. D. Roerdink and A. M. Kroom eds., John Wiley and Sons, Chichester, 1989; "Controlled Release of Biologically Active Agents" Richard Baker, John Wiley and Sons, New York, 1987.

Different kinds of polymers have been used for the above purposes and among these polycarbonates showed appropriate biocompatibility characteristics. Kawaguchi et al. (Chem. Pharm. Bull. vol. 31, n. 4, 1400–1403, 1983) disclose the biodegradability of polyethylene carbonate and polypropylene carbonate tablets and the possibility to obtain biocompatible materials having programmed degradation by suitably admixing the two polycarbonates.

Polycarbonates have been well known for a long time. Aliphatic polycarbonates are well known for example from DE 2546534, published on Apr. 28, 1977, JP 6224190, published on Oct. 22, 1987, JP 1009225, published on Jan. 12, 1989, which provide them as plastifying agents and intermediates for the preparation of polyurethanes (see also U.S. Pat. No. 4,105,641, issued Aug. 8, 1978).

Also polycarbonates having homo- and copolymeric nature have been proposed.

In U.S. Pat. No. 4,716,203 (American Cyanamid), issued on Dec. 29, 1987, diblock and triblock copolymers are disclosed, having a first block of glycolic acid ester linked with trimethylene carbonate; triblock copolymers have an intermediate block obtained from ethylene oxide homopolymer or ethylene oxide-cyclic ether copolymer, otherwise from macrocyclic ether copolymers. Said copolymers are bioabsorbable and are indicated for the final finishing of synthetic surgical threads.

International Patent Application WO 8905664 (Allied-Signal Inc.), published on Jun. 29, 1989, discloses medical devices partly or wholly formed by polycarbonates homopolymers or copolymers, which may contain polyether-polyamino moieties in the polymeric chain.

EP-A-0427185 (Boehringer Ingelheim), published on Jan. 15, 1991, discloses copolymers obtained from trimethylene carbonate and optically inactive lactides, useful for the manufacturing of surgical grafts. Chemically, the copolymers disclosed by Boehringer are polyesterpolycarbonates and are obtained by two distinct processes: a one-step process, resulting in random copolymers, and a two-step process, resulting in block copolymers. The block copolymers consist of a polycarbonate block, resulting from the first process step, which a second polyester block is linked to (see Example 17). The resulting basic structure is described by the following formula (A)

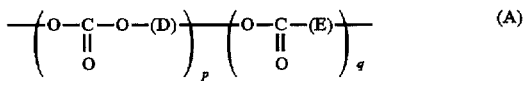

wherein D and E are hydrocarbon residues, p and q indicate the length of the block. By comparing formula (A) and formula (I) of the present invention, the different distribution of the carbonic and carboxylic ester functions in the polymeric structures can be observed.

International Patent Application WO 9222600, published on Dec. 23, 1992, in the applicant's name, discloses randomized polyesterpolycarbonate block copolymers of formula (I) useful as bioerosible matrices. But the copolymers therein disclosed are not capable of achieving molecular weight and viscosity higher than a determined value, thus limiting their use as bioerosible matrices, making the workability difficult. The copolymers disclosed in this reference are prepared starting from a mixture containing the hydroxyacids necessary for the formation of the polyester block and a determined amount of a diol as to obtain a polyester oligomer bearing two hydroxylic functions at its ends. The resulting intermediate is then reacted with carbonyldiimidazole, giving the corresponding diimidazolyl formate, which is then reacted with the desired diol to obtain the final polycarbonate. Through this process it is possible to obtain copolymers having a maximum viscosity of 0.45 dl/g (see Examples), but it is not possible to achieve higher values.

It has now been found that by means of a new process it is possible to obtain copolymers of formula (I) having viscosities higher than 0.45 dl/g.

Such a process is a further object of the present invention, together with the high molecular weight polymers obtained therefrom. The present invention is therefore a selection invention of WO 9222600.

In a first embodiment of the present invention, said process comprises:

a) reaction under vacuum of a mixture of hydroxyacids of formula (IV) and (V)

$$HO-R_3-\overset{O}{\underset{\|}{C}}-OH \quad \text{and} \quad HO-R_4-\overset{O}{\underset{\|}{C}}-OH$$

(IV) (V)

wherein $R_3$ and $R_4$ are as defined above, to give the polyester oligomer (VI)

$$H(-O-R_3-\overset{O}{\underset{\|}{C}})_x(-O-R_4-\overset{O}{\underset{\|}{C}})_y-OH \quad (VI)$$

wherein $R_3$, $R_4$, x and y are as defined above;

b) reaction of the polyester (VI) with bis-chloroformate of formula (VIII)

$$Cl-\overset{O}{\underset{\|}{C}}-O-R_5-O-\overset{O}{\underset{\|}{C}}-Cl \quad (VIII)$$

wherein $R_5$ is as defined above; optionally in the presence of a tertiary amine, at a temperature ranging from $-10°$ to $50°$ C.; preferably from $0°$ to $30°$ C.; and subsequent application of vacuum (pressure from 5 to 0.001 mmHg, preferably from 1 to 0.1 mmHg).

According to this first embodiment of the invention, high molecular weight polyesterpolycarbonates of formula (I), having viscosity higher than 0.45 dl/g, are obtained.

The starting materials are commercially available, anyway they are described in the chemical literature.

The preparation of the polyester (VI) occurs under inert atmosphere, for example in an inert gas, such as nitrogen or argon, at a temperature ranging from $170°$ to $220°$ C.; preferably from $180°$ to $200°$ C.; for a time of 15–30 hours, preferably 20–25 hours. After that, an in vacuo reaction step follows at a vacuum value of 5 to 0.001 mmHg, preferably less than 1 mmHg, for the same time and at the same temperature.

After in vacuo step, the oligomer is cooled while maintaining vacuum and it is isolated by precipitation from chloroform/ethyl ether.

Subsequently, the oligomer is reacted with the bischloroformate (VIII) in a chlorinated solvent at a temperature ranging from $0°$ C. to room temperature, optionally in the presence of a tertiary amine, for a period of time ranging from 4 to 30 hours, preferably 15–20 hours.

According to a second embodiment of the present invention, the process comprises the in situ formation of the bischloroformate by reacting phosgene with a diol of formula (X)

$$HO-R_5-OH \quad (X)$$

wherein $R_5$ is as above defined, to give the corresponding bischloroformate, which is then reacted with a polyester oligomer of formula (VI)

$$H(-O-R_3-\overset{O}{\underset{\|}{C}})_x(-O-R_4-\overset{O}{\underset{\|}{C}})_y-OH \quad (VI)$$

wherein $R_3$, $R_4$, x and y are as defined above, optionally in the presence of one or more tertiary amines, and a subsequent in vacuo application step to give the polymer of formula (I).

According to a third embodiment of the present invention, a polyester oligomer of formula (VI)

$$H(-O-R_3-\overset{O}{\underset{\|}{C}})_x(-O-R_4-\overset{O}{\underset{\|}{C}})_y-OH \quad (VI)$$

wherein $R_3$, $R_4$, x and y are as defined above, is reacted with phosgene to give chloroformate of formula (IX), $$Cl-CO(O-R_3-\overset{O}{\underset{\|}{C}})_x(-O-R_4-\overset{O}{\underset{\|}{C}})_y-Cl \quad (IX)$$

wherein $R_3$ and $R_4$ are as defined above, which is then reacted with a diol of formula (X)

$$HO-R_5-OH \quad (X)$$

wherein $R_5$ is as above defined, to give the polymer of formula (I).

Preferably, the reaction between (VI) and (IX) is carried out in the presence of a tertiary amine.

The final polymerization step is carried out under the same conditions as above.

In a further preferred embodiment of the present invention, in the polyesterpolycarbonates of formula (I), the polyester residue of formula (II) is a lactic acid-glycolic acid polyester in 1:1 molar ratio; $R_1$ and $R_2$ are alkylene chains having from 2 to 12 carbon atoms.

Advantageously, the process according to the present invention allows also the preparation of low molecular weight polyesterpolycarbonates disclosed in WO 9222600.

The polymers obtainable by the process of the present invention have high viscosity, higher than that of the polymers disclosed in WO 9222600.

The polymers of the present invention have advantageous physico-chemical properties which make them suitable for use as bioerosible matrices. Particularly, these polymers have low crystallinity and such a property gives them good biodegradability and workability characteristics, in particular in the coextrusion technology.

Therefore, the use of the above described polyesterpolycarbonates for the preparation of bioerosible matrices is another object of the present invention.

In another aspect thereof, the present invention provides pharmaceutical compositions for the controlled release of the active principle from bioerosible matrices comprising polyesterpolycarbonates of formula (I).

The following examples further illustrate the invention.

EXAMPLE 1

243.33 g of a 72% lactic acid aqueous solution and 151.15 g of 99% glycolic acid were placed into a three-necked flask, equipped with a Dean-Starck apparatus, under anhydrous nitrogen atmosphere. The mixture was maintained under nitrogen stream and stirred at the temperature of $200°$ C. for 24 hours. Vacuum was then applied (<1 mmHg) for 24 hours at the same temperature. After cooling under vacuum, dissolving in chloroform (2 ml of chloroform per g of polymer) and precipitating in ethyl ether, 266.77 g of oligomer were thus obtained with a number-average molecular weight 1,870 (evaluated by titration in benzyl alcohol with a 0.1N standard solution of tetrabutylammonium hydroxide in isopropanol) and an intrinsic viscosity of 0.105 dl/g.

EXAMPLE 2

With a procedure similar to the one of example 1, 243.33 g of a 72% lactic acid aqueous solution and 50.38 g of 99% glycolic acid were reacted. 169.88 g of oligomer were thus obtained with a number-average molecular weight 2560 (evaluated by titration in benzyl alcohol with a 0.1N standard solution of tetrabutylammonium hydroxide in isopropanol) and an intrinsic viscosity of 0.13 dl/g (chloroform at 32° C.).

EXAMPLE 3

With a procedure similar to the one of example 1, 243.33 g of a 72% lactic acid aqueous solution were reacted. 102 g of oligomer were thus obtained with a number-average molecular weight 2320 (evaluated by titration in benzyl alcohol with a 0.1N standard solution of tetrabutylammonium hydroxide in isopropanol) and an intrinsic viscosity of 0.12 dl/g (chloroform at 32° C.).

EXAMPLE 4

243.33 g of a 72% lactic acid aqueous solution and 151.15 g of 99% glycolic acid were placed into a three-necked flask, equipped with a Dean-Starck apparatus, under anhydrous nitrogen atmosphere. The mixture was maintained under nitrogen stream and stirred at the temperature of 200° C. for 24 hours. After cooling under vacuum, dissolving in chloroform (2 ml of chloroform per g of polymer) and precipitating in ethyl ether, 244.5 g of oligomer were thus obtained with a number-average molecular weight 455 (evaluated by titration in benzyl alcohol with a 0.1N standard solution of tetrabutylammonium hydroxide in isopropanol).

EXAMPLE 5

49.44 g of a oligomer, a 1:1 molar ratio lactic acid-glycolic acid copolymer (PLGA 1:1), having number-average molecular weight 1,873 (intrinsic viscosity of 0.096 dl/g) and 81.4 ml of amylane-stabilized and calcium hydride-dried chloroform were placed into a 500 ml two-necked flask, under anhydrous nitrogen atmosphere. After complete dissolution of the oligomer, N-ethyldiisopropylamine (98% w/w titre) and 3.29 g of 4-dimethylaminopyridine ( 99% w/w titre ) were added. After cooling the mixture to 0° C., 5.64 ml of triethylene glycol bischloroformate (97% w/w titre) were dropped within 5 minutes. The mixture was maintained at 0° C. for 4 hours, then warmed to room temperature (20°–25° C.) within two hours, and kept at this value for further 10 hours. A concentration step of the reaction medium was then carried out by evaporating off the solvent under vacuum (<1 mmHg, T-20° C., 2 hours). The resulting solid was taken up with chloroform and precipitated in ethyl ether. After a further precipitation of the polymer in isopropyl alcohol and extraction in isopropyl ether, 45 g of a polymer having intrinsic viscosity of 0.729 dl/g at 32° C. in chloroform were obtained.

EXAMPLE 6

With a procedure similar to the one of example 5, 49.94 g of a oligomer, a 1:1 molar ratio lactic acid-glycolic acid copolymer (PLGA 1:1), having number-average molecular weight 1,873 (intrinsic viscosity of 0.096 dl/g) and 6.48 g of 1,6-hexanediol bischloroformate (97% w/w titre) were reacted. 47.5 g of a polymer having intrinsic viscosity of 0.576 dl/g were obtained.

EXAMPLE 7

With a procedure similar to the one of example 5, 49.94 g of a oligomer, a 1:1 molar ratio lactic acid-glycolic acid copolymer (PLGA 1:1), having number-average molecular weight 1,873 (intrinsic viscosity of 0.096 dl/g) and 5.74 g of 1,4-butanediol bischloroformate were reacted. 48.25 g of a polymer having intrinsic viscosity of 0.626 dl/g were obtained.

EXAMPLE 8

With a procedure similar to the one of example 5, 49.94 g of a oligomer, a 1:1 molar ratio lactic acid-glycolic acid copolymer (PLGA 1:1), having number-average molecular weight 1,873 (intrinsic viscosity of 0.096 dl/g) and 8.51 g of tetraethylene glycol bischloroformate were reacted. 49.3 g of a polymer having intrinsic viscosity of 0.727 dl/g were obtained.

EXAMPLE 9

With a procedure similar to the one of example 5, 49.94 g of a oligomer, a 3:1 molar ratio lactic acid-glycolic acid copolymer (PLGA 3:1), having number-average molecular weight 1,905 (intrinsic viscosity of 0.102 dl/g) and 8.55 g of tetraethylene glycol bischloroformate were reacted. 50.4 g of a polymer having intrinsic viscosity of 0.675 dl/g were obtained.

EXAMPLE 10

With a procedure similar to the one of example 5, 49.94 g of a oligomer, a 1:1 molar ratio lactic acid-glycolic acid copolymer (PLGA 1:1), having number-average molecular weight 1,873 ( intrinsic viscosity of 0.096 dl/g) and 6.16 g of diethylene glycol bischloroformate were reacted. 47.5 g of a polymer having intrinsic viscosity of 0.658 dl/g were obtained.

EXAMPLE 11

With a procedure similar to the one of example 5, 49.94 g of a oligomer, a 1:1 molar ratio lactic acid-glycolic acid copolymer (PLGA 1:1), having number-average molecular weight 1,873 (intrinsic viscosity of 0.096 dl/g) and 14.0 g of polyethylene glycol 400 bischloroformate were reacted. 52.4 g of a polymer having intrinsic viscosity of 0,582 dl/g were obtained.

EXAMPLE 12

With a procedure similar to the one of example 5, 49.94 g of a oligomer, a 1:1 molar ratio lactic acid-glycolic acid copolymer (PLGA 1:1), having number-average molecular weight 1,873 (intrinsic viscosity of 0.096 dl/g) and 19.33 g of polyethylene glycol 600 bischloroformate were reacted. 58.5 g of a polymer having intrinsic viscosity of 0.527 dl/g were obtained.

EXAMPLE 13

15 g of PLGA 1:1 (number-average molecular weight 1,565) and 27.25 ml of chloroform were placed into a 250 ml two-necked flask, under anhydrous nitrogen atmosphere.

After cooling the mixture at 0° C., 16.67 ml of a toluene solution of phosgene (1.93M) were added. After three hours at 0° C., 1.1 ml of tetraethylene glycol, 2.81 ml of N-ethyldiisopropylamine and 0.993 g of 4-dimethylaminopyridine were added. After two hours the temperature was warmed to 25° C. and kept at this value for 14 hours. The reaction mixture was then concentrated for 2 hours under vacuum (<1 mmHg), taken up with 20 ml of chloroform and precipitated in ethyl ether. 14.2 g of a polymer having viscosity of 0.12 dl/g were obtained.

EXAMPLE 14

21.74 ml of a toluene solution of phosgene (1.93M) were introduced in a three-necked flask, equipped with a dropping funnel, under anhydrous nitrogen atmosphere. After cooling down to 0° C., a solution containing 2.24 ml of triethylene glycol, 9 ml of chloroform, 5.74 ml of N-ethyldiisopropylamine and 2:02 g of 4-dimethylaminopyridine was dropped therein. After 20 minutes phosgene excess was removed by bubbling nitrogen, and a solution containing PLGA 1:1 (number-average molecular weight 1,865, intrinsic viscosity of 0.099 dl/g), 54.9 ml of chloroform, 5.74 ml of N-ethyldiisopropylamine and 2.02 g of 4-dimethylaminopyridine was dropped therein. The mixture was maintained at 0° C. for 4 hours, then warmed to room temperature, and kept at this value for 12 hours. The reaction mixture was then concentrated for 4 hours under vacuum (<1 mmHg), taken up with chloroform and precipitated in ethyl ether. After a further precipitation in isopropyl alcohol and extraction in isopropyl ether, 29.5 g of a polymer having intrinsic viscosity of 0.782 were obtained.

EXAMPLE 15

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 1.90 g of 1,6-hexanediol were reacted. 28.5 g of a polymer having intrinsic viscosity of 0.543 dl/g were obtained.

EXAMPLE 16

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 1.44 g of 1,4-butanediol were reacted. 26.9 g of a polymer having intrinsic viscosity of 0.631 dl/g were obtained.

EXAMPLE 17

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 3.12 g of tetraethylene glycol were reacted. 27.4 g of a polymer having intrinsic viscosity of 0.758 dl/g were obtained.

EXAMPLE 18

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 1.70 g of diethylene glycol were reacted. 27.2 g of a polymer having intrinsic viscosity of 0. 697 dl/g were obtained.

EXAMPLE 19

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 6.43 g of polyethylene glycol 400 were reacted. 30.5 g of a polymer having intrinsic viscosity of 0.689 dl/g were obtained.

EXAMPLE 20

With a procedure similar to the one of example 14, 30 g of a oligomer, a 1:1 molar ratio lactic acid-glycolic acid copolymer (PLGA 1:1), having number-average molecular weight 1,865 (intrinsic viscosity of 0.097 dl/g) and 9.65 g of polyethylene glycol 600 were reacted. 35.8 g of a polymer having intrinsic viscosity of 0.624 dl/g were obtained.

EXAMPLE 21

With a procedure similar to the one of example 14, 30 g of a oligomer, a 1:1 molar ratio lactic acid-glycolic acid copolymer (PLGA 1:1), having number-average molecular weight 1,920 (intrinsic viscosity of 0.098 di/g) and 15.62 g of polyethylene glycol having average molecular weight 1,000 were reacted. 44 g of a polymer having number-average molecular weight 239,000, weight-average molecular weight 434,000 (values referred to the polystyrene standards in chloroform) and an intrinsic viscosity of 1.740 dl/g were obtained.

EXAMPLE 22

With a procedure similar to the one of example 14, 30 g of a oligomer, a 1:1 molar ratio lactic acid-glycolic acid copolymer (PLGA 1:1), having number-average molecular weight 1,920 (intrinsic viscosity of 0.098 dl/g) and 31.25 g of polyethylene glycol having average molecular weight 2,000 were reacted. 60 g of a polymer having number-average molecular weight 197,000, weight-average molecular weight 37,0000 (values referred to the polystyrene standards in chloroform) and an intrinsic viscosity of 1.552 dl/g were obtained.

EXAMPLE 23

With a procedure similar to the one of example 14, 20 g of a oligomer, a 1:1 molar ratio lactic acid-glycolic acid copolymer (PLGA 1:1), having number-average molecular weight 1,920 (intrinsic viscosity of 0.098 dl/g) and 41.60 g of polyethylene glycol having average molecular weight 4,000 were reacted. 60.5 g of a polymer having number-average molecular weight 194,000, weight-average molecular weight 370,000 (values referred to the polystyrene standards in chloroform) and an intrinsic viscosity of 2.161 dl/g were obtained.

EXAMPLE 24

With a procedure similar to the one of example 14, 10 g of a oligomer, a 1:1 molar ratio lactic acid-glycolic acid copolymer (PLGA 1:1), having number-average molecular weight 1,920 (intrinsic viscosity of 0.098 dl/g) and 41.60 g of polyethylene glycol having average molecular weight 8,000 of were reacted. 50 g of a polymer having number-average molecular weight 110,000, weight-average molecular weight 276,000 (values referred to the polystyrene standards in chloroform) and an intrinsic viscosity of 1.162 dl/g were obtained.

EXAMPLE 25

With a procedure similar to the one of example 14, 30 g of a oligomer, a 1:1 molar ratio 1 actic acid-glycolic acid copolymer (PLGA 1:1), having number-average molecular weight 1,920 (intrinsic viscosity of 30 0.098 dl/g) and 15.62 g of polytetrahydrofuran having average molecular weight 1,000 were reacted. 44 g of a polymer having an intrinsic viscosity of 0.600 dl/g were obtained.

EXAMPLE 26

With a procedure similar to the one of example 14, 20 g of a oligomer, a 1:1 molar ratio lactic acid-glycolic acid copolymer (PLGA 1:1), having number-average molecular weight 1,920 (intrinsic viscosity of 0.098 dl/g) and 41.60 g of polypropylene glycol having average molecular weight 4,000 were reacted. 60.0 g of a polymer having an intrinsic viscosity of 0.25 dl/g were obtained.

EXAMPLE 27

Microspheres of the oligomer having number-average molecular weight 1,920 were prepared according to the following procedure. 0.60 g of polymer were dissolved in 8 ml of chloroform. The solution was slowly added to a 0.4% aqueous solution of polyvinyl alcohol having average molecular weight 20,000 the system was kept under stirring, at room temperature, for 2 hours with stirring rate of 750 rpm. The final product was sieved humid. 120 mg of microspheres were obtained, having a granulometry of 68–125 micrometers.

EXAMPLE 28

With a procedure similar to the one of example 27, 95 mg of microspheres were prepared, having granulometry from 68 to 125 micrometers, of a commercial polyester having the following characteristics: 75:25 D,L-lactic acid/glycolic acid ratio, number-average molecular weight 53,000, weight-average molecular weight 105,000 and intrinsic viscosity of 0.54 dl/g.

EXAMPLE 29

With a procedure similar to the one of example 27, 142 mg of microspheres were prepared, having granulometry from 68 to 125 micrometers, of the product obtained with the procedure of example 21.

EXAMPLE 30

With a procedure similar to the one of example 27, 222 mg of microspheres were prepared, having granulometry from 68 to 125 micrometers, of the product obtained with the procedure of example 22.

EXAMPLE 31

With a procedure similar to the one of example 27, 330 mg of microspheres were prepared, having granulometry from 68 to 125 micrometers, of the product obtained with the procedure of example 23.

EXAMPLE 32

With a procedure similar to the one of example 27, 58 mg of microspheres were prepared, having granulometry from 68 to 125 micrometers, of the product obtained with the procedure of example 14.

EXAMPLE 33

Degradation of the microspheres prepared according to examples 28–33 was evaluated placing microspheres samples (160 mg) into 5 ml of phosphate buffer, pH-7.4, at a temperature of 37° C., checking the complete disappearance thereof by optical microscopy. The obtained data are summarized in the following Table.

TABLE

| Polymer | Days on which the microspheres disappear completely |
|---|---|
| Commercial PLGA | >32 |
| Polymer of example 21 | >32 |
| Polymer of example 22 | 7 |
| Polymer of example 23 | 4 |
| Polymer of example 14 | >32 |
| Oligomer with MW - 1,920 | 11 |

The Table shows that according to the process of the invention copolymers having degradation times ranging within wide time intervals can be obtained. Such intervals range from a few days to values comparable with those of commercial copolyesters, thus allowing to prepare systems having optimum degradation rates, depending on the application requirements.

We claim:

1. A polyesterpolycarbonates of formula (I)

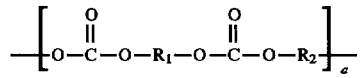

wherein a is an integer from 2 to 300; $R_1$ and $R_2$, which can be the same or different, are each a polyester residue of formula (II)

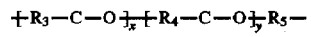

wherein x and y are integers from 0 to 100, the ratio (x/x+y)*100, being comprised between 0 and 100, with the proviso that x and y are not 0 at the same time; $R_3$ and $R_4$, which can be the same or different, are each a straight or branched chain aliphatic hydrocarbon residue having from 1 to 4 carbon atoms; $R_5$ is a straight or branched chain aliphatic hydrocarbon residue having from 2 to 18 carbon atoms or a cycloaliphatic hydrocarbon residue having from 3 to 8 carbon atoms, optionally bearing one or more straight or branched alkyl substituents; or a polyoxyalkylene residue of formula (III):

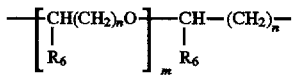

wherein: $R_6$ is hydrogen or methyl, n is an integer from 1 to 3 and m is an integer from 1 to 200; the two —$R_3$—COO and —$R_4$—COO groups being randomly distributed in the polyester residue, with the polyesterpolycarbonates of formula (I) having an intrinsic viscosity of greater than 0.45 dl/g when measured in chloroform at 32° C.

2. A polyesterpolycarbonate according to claim 1, wherein the polyester residue of formula (II) is a lactic acid-glycolic acid polyester in 1:1 molar ratio.

3. A polyesterpolycarbonate according to claim 1, wherein the intrinsic viscosity is at least about 1.162 dl/g.

4. A polyesterpolycarbonate according to claim 1, wherein the intrinsic viscosity is at least about 2.161 dl/g.

5. A polyesterpolycarbonate according to claim 1, wherein the x and y are each at least 1.

6. A process for the preparation of polyesterpolycarbonates of formula (I)

$$-\left[O-\overset{O}{\underset{\|}{C}}-O-R_1-O-\overset{O}{\underset{\|}{C}}-O-R_2\right]_a-$$

wherein a is an integer from 2 to 300; $R_1$ and $R_2$, which can be the same or different, are each a polyester residue of formula (II)

$$+R_3-C-O\}_x+R_4-C-O\}_y R_5-$$

wherein x and y are integers from 0 to 100, the ratio $(x/x+y)*100$, being comprised between 0 and 100, with the proviso that x and y are not 0 at the same time; $R_3$ and $R_4$, which can be the same or different, are each a straight or branched chain aliphatic hydrocarbon residue having from 1 to 4 carbon atoms; $R_5$ is a straight or branched chain aliphatic hydrocarbon residue having from 2 to 18 carbon atoms or a cycloaliphatic hydrocarbon residue having from 3 to 8 carbon atoms, optionally bearing one or more straight or branched alkyl substituents; or a polyoxyalkylene residue of formula (III):

$$-\left[\underset{R_6}{CH(CH_2)_nO}\right]_m-\underset{R_6}{CH}-(CH_2)_n-$$

wherein: $R_6$ is hydrogen or methyl, n is an integer from 1 to 3 and m is an integer from 1 to 200; the two —$R_3$—COO and —$R_4$—COO groups being randomly distributed in the polyester residue, the method comprising the following steps:

a) reacting under vacuum a mixture of hydroxyacids of formula (IV) and (V)

$$HO-R_3-\overset{O}{\underset{\|}{C}}-OH \quad \text{and} \quad HO-R_4-\overset{O}{\underset{\|}{C}}-OH$$

(IV) (V)

wherein $R_3$ and $R_4$ are as defined above, giving the polyester oligomer (VI)

$$H+O-R_3-\overset{O}{\underset{\|}{C}}\}_x+O-R_4-\overset{O}{\underset{\|}{C}}\}_y OH$$

wherein $R_3$ and $R_4$, x and y are as defined above;

b) reacting polyester (VI) with bis-chloroformate of formula (VIII)

$$Cl-\overset{O}{\underset{\|}{C}}-O-R_5-O-\overset{O}{\underset{\|}{C}}-Cl$$

wherein $R_5$ is as defined above; optionally in the presence of one or more tertiary amines, and a subsequent vacuum application step.

7. A process according to claim 6, wherein a diol of formula (X)

$$HO-R_5-OH$$

wherein $R_5$ is as defined above, is reacted with phosgene to produce a corresponding bis-chloroformate, which is then reacted with a polyester oligomer of formula (VI)

$$H+O-R_3-\overset{O}{\underset{\|}{C}}\}_x+O-R_4-\overset{O}{\underset{\|}{C}}\}_y OH$$

wherein $R_3$, $R_4$, X and y are as defined above, optionally in the presence of one or more tertiary amines and a subsequent vacuum application step, to produce the polymer of formula (I).

8. A process according to claim 6 wherein a polyester oligomer of formula (VI)

$$H+O-R_3-\overset{O}{\underset{\|}{C}}\}_x+O-R_4-\overset{O}{\underset{\|}{C}}\}_y OH$$

wherein $R_3$, $R_4$, x and y are as defined above, is reacted with phosgene to give the chloroformate of formula (IX), $$Cl-CO(O-R_3-\overset{O}{\underset{\|}{C}}\}_x+O-R_4-\overset{O}{\underset{\|}{C}}\}_y Cl$$

wherein $R_3$ and $R_4$ are as defined above, which is then reacted with a diol of formula $$HO-R_5-OH$$

wherein $R_5$ is as defined above, to produce the polymer of formula (I).

9. A polyesterpolycarbonate obtained by the process of claim 6.

10. A bioerosible matrix comprising a polyesterpolycarbonate according to claim 9 and an active principle.

11. A pharmaceutical product comprising microspheres of the bioerosible matrix according to claim 10.

12. A bioerosible matrix comprising a polyesterpolycarbonate according to claim 1 and an active principle.

13. A pharmaceutical product comprising microspheres of the bioerosible matrix according to claim 12.

* * * * *